US00PP19965P2

(12) United States Plant Patent
Hansoti

(10) Patent No.: US PP19,965 P2
(45) Date of Patent: Apr. 28, 2009

(54) ***EPIPREMNUM* PLANT NAMED 'NJOY'**

(50) Latin Name: *Epipremnum pinnatum*
Varietal Denomination: NJOY

(76) Inventor: Ashish Hansoti, 1, Navjivan Bldg, Dattatreya Road, Santa Cruz West, Mumbai, Maharashtra (IN), 400 054

( * ) Notice: Subject to any disclaimer, the term of this patent is extended or adjusted under 35 U.S.C. 154(b) by 0 days.

(21) Appl. No.: 11/978,416

(22) Filed: Oct. 29, 2007

(51) Int. Cl.
*A01H 5/00* (2006.01)

(52) U.S. Cl. ..... Plt./381
(58) Field of Classification Search ..... Plt./263.1, Plt./381, 226
See application file for complete search history.

*Primary Examiner*—Kent L Bell

(57) ABSTRACT

A new and distinct *Epipremnum* cultivar named 'NJOY' is disclosed, characterized by very compact growth, bright, distinctive green and white variegation. Small broad leaves and a compact inflorescence. The new variety is an *Epipremnum*, normally produced as an indoor potted plant.

2 Drawing Sheets

Latin name of the genus and species: *Epipremnum pinnatum.*
Variety denomination: 'NJOY'.

BACKGROUND OF THE INVENTION

The new cultivar is a product of a planned breeding program. The object of the breeding program was to select and reproduce *Epipremnum pinnatum* plants with brighter variegation of the leaves and improved plant forms. The new variety was discovered as a naturally occurring branch mutation in a grouping of more than 100 plants, representing superior clones of the parent variety 'Marble Queen.' Clones were selected for several years, with a selection criteria of shorter internodes and brightest variegation. The new cultivar is a selection from one of these unnamed superior clones of 'Marble Queen,' not directly selected from 'Marble Queen.' The new variety was discovered by Ashish Arvind Hansoti in 2002 at a commercial greenhouse near Mumbai, India.

Asexual reproduction of the new cultivar 'NJOY' by vegetative cuttings was performed at a commercial greenhouse outside of Mumbai, India and has shown that the unique features of this cultivar are stable and reproduced true to type on successive generations. Approximately 25 generations have been reproduced.

SUMMARY OF THE INVENTION

The cultivar 'NJOY' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NJOY' These characteristics in combination distinguish 'NJOY' as a new and distinct *Epipremnum* cultivar:

1. Small, broad, usually ovate leaves. Some tendency to produce even broader, deltate leaves.
2. Compact growth with very short internodes.
3. Bright, distinct variegation pattern.

4. Characteristic patch of green color, of varying shape and size on either side of the midrib.
5. Green variegation on cream to white background with many shades of green on a single leaf.
6. Stems relatively strong, darker green in overall appearance.

Plants of the new cultivar 'NJOY' are similar to plants of the parent, *Epipremnum pinnatum* 'Marble Queen' unpatented, in most horticultural characteristics, however, plants of the new cultivar 'NJOY' are shorter and produce much shorter internodes than the parent. Additionally, the new variety has smaller leaves, broader leaves, with well-defined, regular variegation. The new variety also produces many shades of green within its variegation, while the parent variety characteristically has no more than 2 shades of green.

The parent variety is the best commercial comparison to the new variety 'NJOY.'

BRIEF DESCRIPTION OF THE PHOTOGRAPH

Figure 1:
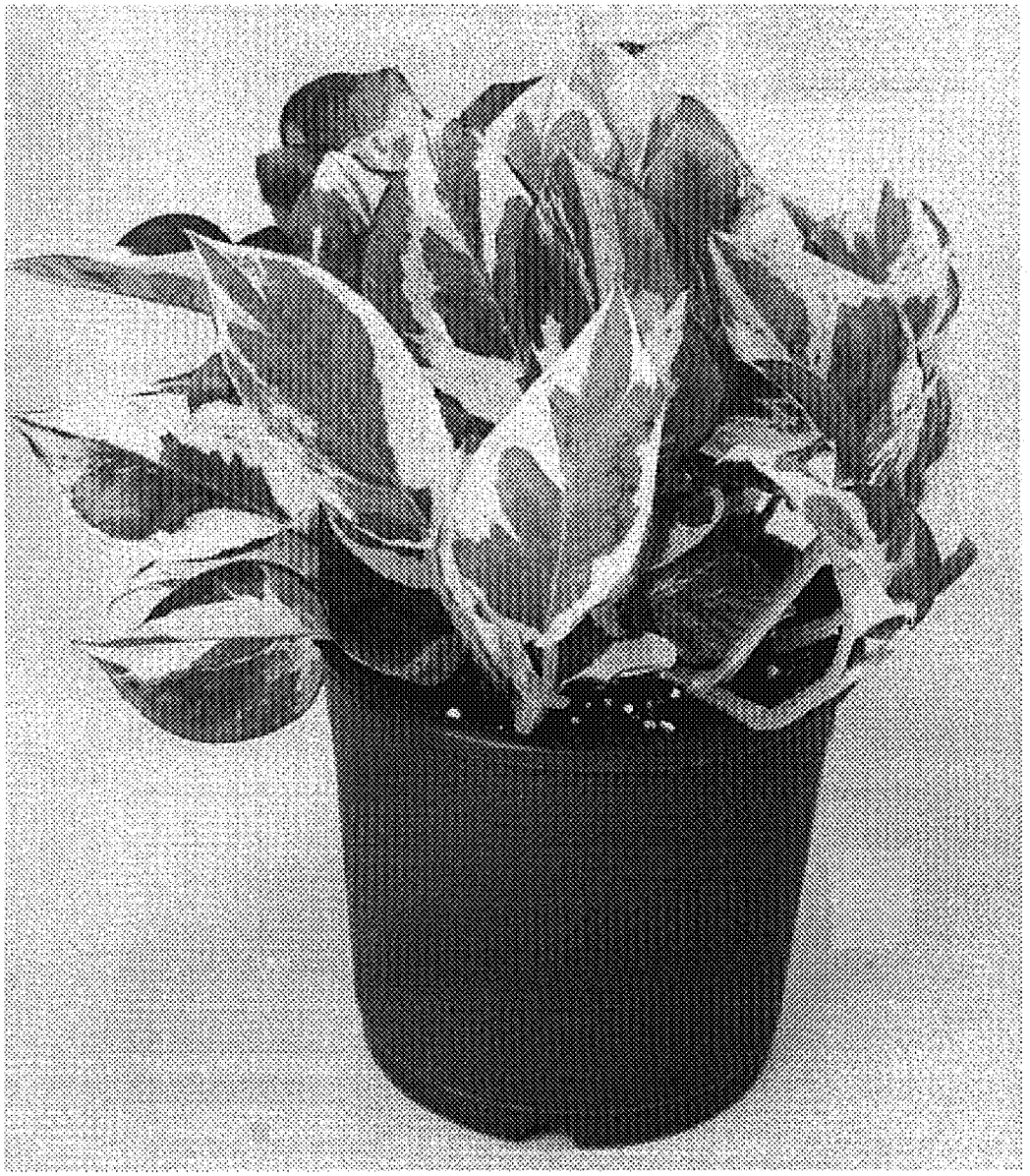

The accompanying photograph in FIG. 1 illustrates in full color a typical plant of 'NJOY' grown in a greenhouse, in a 13 cm pot. Age of the plant photographed is 24 weeks.

Figure 2:
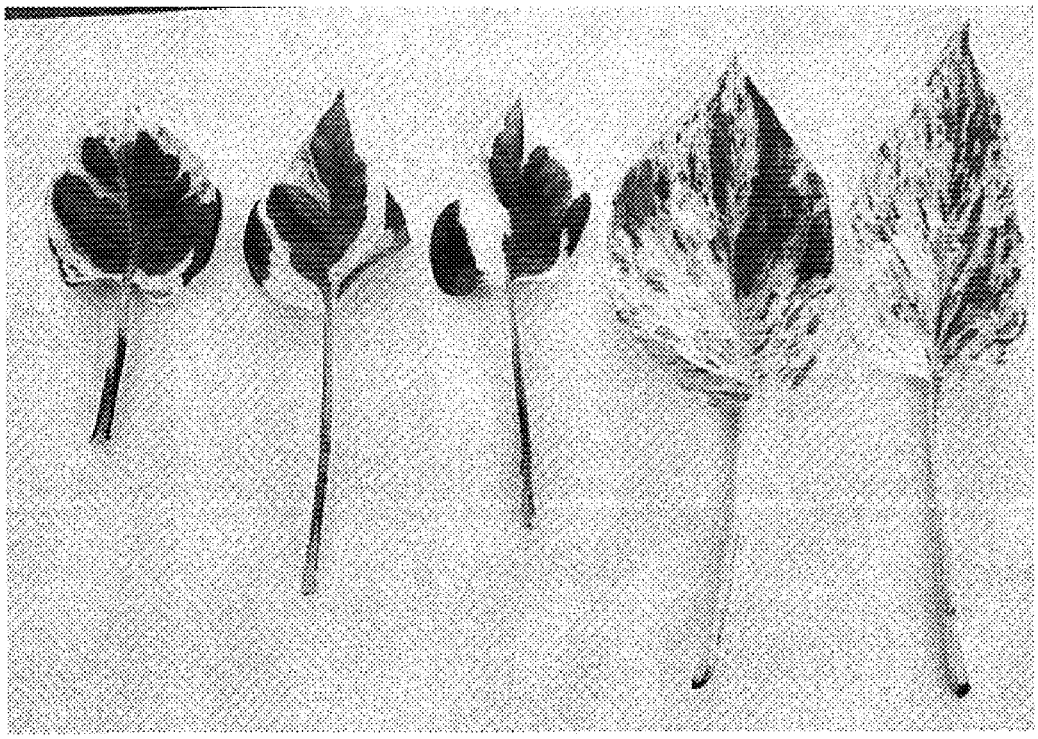

FIG. 2 illustrates in full color mature typical leaves of 'NJOY' grown in a greenhouse, compared to mature leaves of the parent variety 'Marble Queen' grown in a greenhouse.

The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart except where general terms of ordinary dictionary significance are used. The following observations and measurements describe 'NJOY' plants grown in a poly plastic covered greenhouse in Mumbai, India. The greenhouse is covered with an additional shade cloth, allowing 50% natural light through. The growing temperature ranged from 12° C. to 20° C. at night and 20° C. to 35° C. during the day. Light levels were approximately 30–35 LUX. Measurements and numerical values represent averages of typical plant types.

Botanical classification: *Epipremnum pinnatum* cultivar 'NJOY.'

PROPAGATION

Time to Rooting: 20 days under summer conditions of approximately 25° C. to 40° C. 30 to 40 days under winter conditions of approximately 15° C. to 25° C.

Root Description: Moderately fibrous. Aerial roots occasional seen under conditions of high humidity.

PLANT

Growth Habit: Compact, Semi-Trailing tender annual.
Height: Approximately 15 to 25 cm above a 13 cm pot.
Plant Spread: Approximately 30 cm.
Growth Rate: Rapid.
Branching Characteristics: Clusters of short new shoots are formed in the center of the plant, becoming short, trailing branches with age. Very free branching.
Length of Lateral Branches: Approximately 10 cm.
Number of Leaves per Lateral Branch: Approximately 10.
Age of Plant Described: Approximately 22 weeks.

FOLIAGE

Leaf:
*Arrangement.*—Alternate.
*Average length.*—Approximately 5.6 cm.
*Average width.*—Approximately 4.1 cm.
*Shape of blade.*—Ovate, occasionally Deltate.
*Apex.*—Acuminate.
*Base.*—Subcordate.
*Attachment.*—Stalked.
*Margin.*—Entire.
*Texture of top surface.*—Smooth, waxy.
*Texture of bottom surface.*—Somewhat leathery.
*Leaf internode length.*—Approximately 0.5 cm.
*Color.*—Young foliage upper side: Variegated, background near 1D, patches of different shades of green including 137A, 137B, 137D and 193C. Young foliage under side: Variegated, background Near 1D, patches of 137C, 138C and 144B. Mature foliage upper side: Variegated, background somewhat whiter than 155C with different shades of green including 137A, 191A and 188B to 188C. Mature foliage under side: Variegated, on a background somewhat whiter than 155D with different shades of green including 137B and 191A.
*Venation.*—Type: Reticulate. Venation color upper side: Inconspicuous. Venation color under side: Prominent mid-rib is near 138B. Finer veins near 155D.

Petiole:
*Average length.*—Approximately 5.2 cm.
*Color.*—Near 144D.
*Diameters.*—Approximately 0.2 cm.
*Texture.*—Smooth.

FLOWER

Blooming not observed on the new cultivar.

OTHER CHARACTERISTICS

Disease Resistance: Neither resistance nor susceptibility to diseases or pests has been observed in this variety.

Drought Tolerance and Cold Tolerance: Tender annual. Tolerates low temperatures to 6° C. without damage. Tolerant of high humidity and temperatures to 40° C. with shade. No drought tolerance has been observed.

Fruit/Seed Production: Not observed.

What is claimed is:

1. A new and distinct cultivar of *Epipremnum* plant named 'NJOY' as herein illustrated and described.

* * * * *

'NJOY' 13cm pot
24 weeks

Foliage of 'NJOY'

Foliage of 'Marble Queen'